United States Patent
Cottone, Jr.

[11] Patent Number: 5,824,043
[45] Date of Patent: Oct. 20, 1998

[54] ENDOPROSTHESIS HAVING GRAFT MEMBER AND EXPOSED WELDED END JUNCTIONS, METHOD AND PROCEDURE

[75] Inventor: Robert J. Cottone, Jr., Fort Lauderdale, Fla.

[73] Assignee: Cordis Corporation, Miami Lakes, Fla.

[21] Appl. No.: 652,297

[22] Filed: May 23, 1996

Related U.S. Application Data

[62] Division of Ser. No. 208,612, Mar. 9, 1994, Pat. No. 5,549,663.

[51] Int. Cl.$^6$ ............................................. A61F 2/06
[52] U.S. Cl. .......................... 623/1; 606/195; 29/419.1; 228/173.5
[58] Field of Search ................... 29/419.1, DIG. 48; 228/173.5; 623/1, 12; 606/108, 194, 195, 198

[56] References Cited

U.S. PATENT DOCUMENTS

| | | | |
|---|---|---|---|
| 4,475,972 | 10/1984 | Wong . | |
| 4,503,569 | 3/1985 | Dotter . | |
| 4,731,073 | 3/1988 | Robinson | 623/1 |
| 4,738,740 | 4/1988 | Pinchuk et al. . | |
| 4,800,832 | 1/1989 | Gianturco | 128/343 |
| 4,856,516 | 8/1989 | Hillstead | 128/343 |
| 4,886,062 | 12/1989 | Wiktor | 128/343 |
| 4,913,141 | 4/1990 | Hillstead | 606/108 |
| 4,994,071 | 2/1991 | MacGregor | 606/194 |
| 5,015,253 | 5/1991 | MacGregor | 623/1 |
| 5,019,090 | 5/1991 | Pinchuk | 606/194 |
| 5,092,877 | 3/1992 | Pinchuk | 623/1 |
| 5,104,399 | 4/1992 | Lazarus | 623/1 |
| 5,133,732 | 7/1992 | Wiktor | 606/195 |
| 5,217,487 | 6/1993 | Tower | 623/1 |
| 5,226,913 | 7/1993 | Pinchuk | 623/1 |
| 5,282,823 | 2/1994 | Schwartz et al. | 623/1 |
| 5,304,200 | 4/1994 | Spaulding | 623/1 |
| 5,314,472 | 5/1994 | Fontaine | 623/1 |
| 5,354,309 | 10/1994 | Schrepp-Pesch et al. | 623/1 |
| 5,356,423 | 10/1994 | Tihon et al. | 623/1 |
| 5,356,433 | 10/1994 | Rowland et al. | 623/1 |
| 5,360,443 | 11/1994 | Barone et al. | 623/1 |
| 5,443,498 | 8/1995 | Fontaine | 623/1 |

FOREIGN PATENT DOCUMENTS

| | | | |
|---|---|---|---|
| 540290 | 5/1993 | European Pat. Off. | 623/1 |
| 4222380 | 1/1994 | Germany | 623/1 |
| 9505132 | 2/1995 | WIPO | 623/1 |

*Primary Examiner*—John G. Weiss
*Assistant Examiner*—Bruce E. Snow
*Attorney, Agent, or Firm*—Lockwood, Alex, Fitzgibbon & Cummings

[57] ABSTRACT

An endoprosthesis is provided which includes a stent component and a graft component capturing a portion of the stent component. The stent component is made of generally malleable material arranged to provide the stent component with a collapsed transluminal positioning configuration and an expanded, deployed configuration. The stent component has adjacent end windings that are welded together. In a preferred arrangement, a plurality of these welds define a spine-like welded arrangement, and a number of these arrangements are positioned generally circumferentially around the ends of the stent component. The graft component extends generally between the welded end portions of the stent component, with limited overlap being possible. Also provided is a method for forming this endoprosthesis and a procedure by which the endoprosthesis is implanted by deployment with a suitable expansion device.

8 Claims, 1 Drawing Sheet

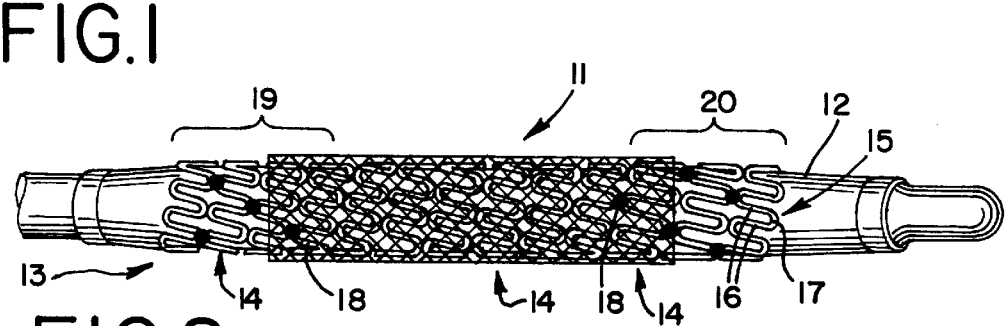
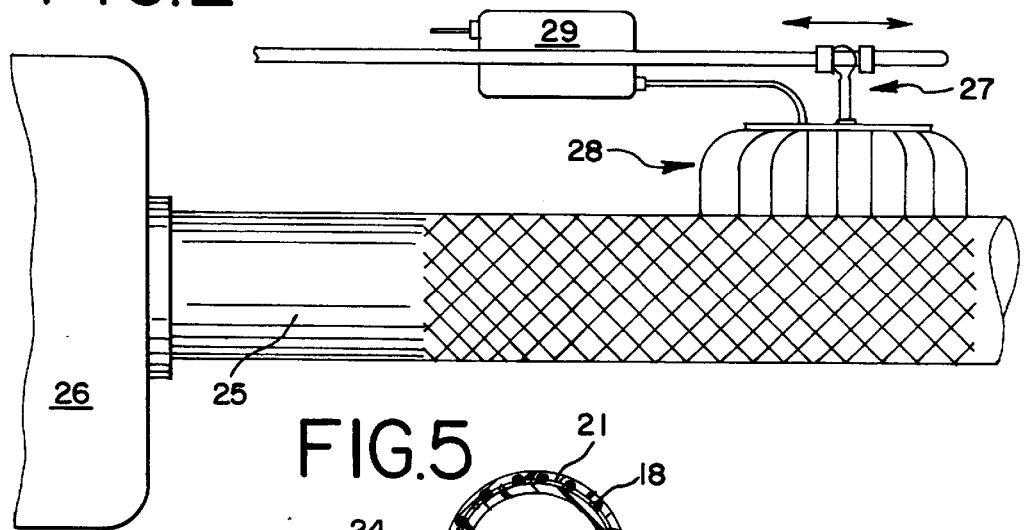
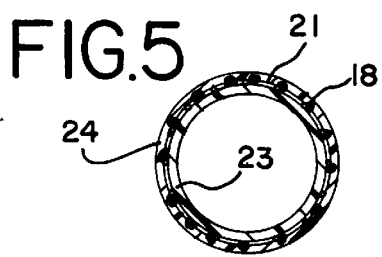
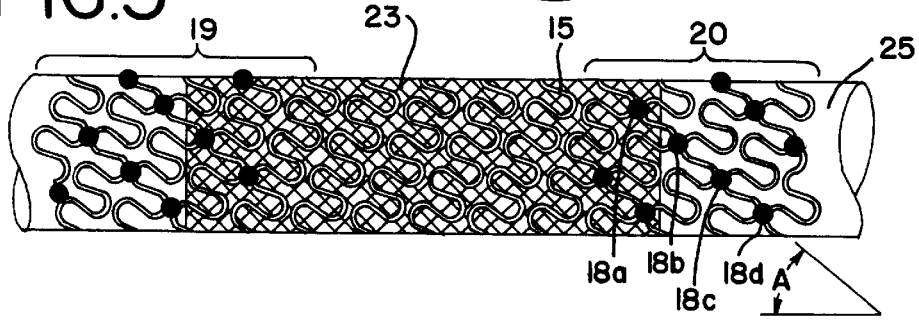
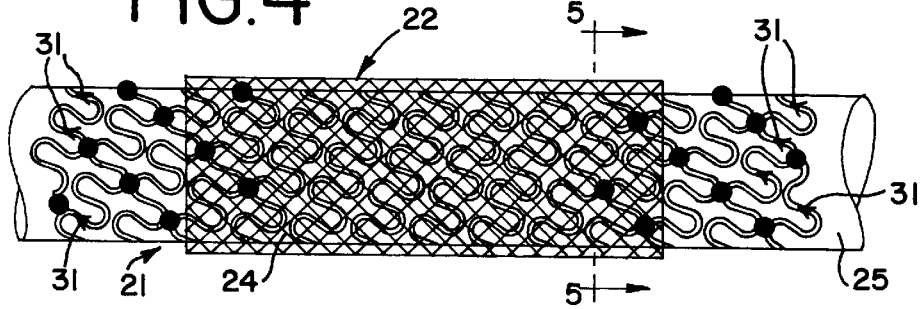

ENDOPROSTHESIS HAVING GRAFT MEMBER AND EXPOSED WELDED END JUNCTIONS, METHOD AND PROCEDURE

This application is a divisional of application Ser. No. 08/208,612, filed Mar. 9, 1994, now U.S. Pat. No. 5,549,663.

BACKGROUND AND DESCRIPTION OF THE INVENTION

The present invention generally relates to endoprostheses and to their preparation and use. More particularly, the invention relates to an endoprosthesis having a stent component with adjacent windings composed of undulating bendable segments that are oriented in a generally helical pattern along the length of the endoprosthesis. The bendable segments impart radial expandability to the endoprosthesis. A number of adjacent windings at each axial end portion of the endoprosthesis are welded together. A graft component closely overlies the outer and inner cylindrical surfaces of the stent component such that the axial end portions of the stent component are uncovered. The welded portions add rigidity to the endoprosthesis ends and assist in maintaining the position and patency of the endoprosthesis after it is deployed within a body vessel.

Various so-called stent devices have been developed or proposed for use in association with angioplasty treatments and other medical treatments or procedures wherein devices having expandable components, such as balloon catheters, are used to treat a condition with a body vessel. The stent is in the nature of a device, usually tubular or cylindrical in shape, which is deployed by a balloon or otherwise and which remains within the vessel at a treatment location upon withdrawal of the balloon catheter or other deployment and/or treatment device. Exemplary patents in this regard include Pinchuk U.S. Pat. Nos. 5,019,090 and No. 5,092,877, MacGregor U.S. Pat. Nos. 4,994,071 and No. 5,015,253, Hillstead U.S. Pat. Nos. 4,856,516 and No. 4,913,141, and Gianturco U.S. Pat. Nos. 4,580,568 and No. 4,800,882 and Wiktor U.S. Pat. No. 4,886,062. Certain endoprosthesis, such as those illustrated in Dotter U.S. Pat. No. 4,503,569, Wallsten U.S. Pat. No. 4,655,771 and Palmaz U.S. Pat. No. 4,733,665 present devices that have no or very limited compliance characteristics. In other stents, concerns can be raised that the body of the endoprosthesis stretches along its longitudinal axis during use. For example, Wiktor U.S. Pat. No. 5,133,732 proposes longitudinal over-stretch limiting means such as by attaching a longitudinal wire generally parallel to the axis of the stent.

Graft devices are also known, grafts being in the nature of woven, wound or molded cylinders or the like that are often used to repair damaged or diseased portions of vessels, such as to repair aneurysms or other vascular or ductal malformations, injuries or diseases. Such grafts provide a replacement wall for the malformed portion, usually implanted during fully invasive surgical procedures. It has been proposed that grafts can be deployed through percutaneous placement by combining the features of a stent-like device with those of a graft. Deployment in this regard would be by way of a percutaneous transluminal angioplasty balloon or other device that can be inserted transluminally and then expanded in place for deployment purposes. One potential difficulty with these types of combination devices is a means for insuring that the graft will remain in place after deployment for extended lengths of time. It is particularly important that any anchoring arrangements also be capable of being accomplished percutaneously and avoid the use of procedures such as suturing, stapling and the like. It is also important that these types of devices experience patency over extended lengths of time.

Endoprostheses in accordance with the present invention combine the ability to be percutaneously and transluminally deployed with excellent patency while also affording good rigidity to certain portions of the stent component in order to enhance the anchoring attributes of the stent-like components of the device. Endoprostheses of the present invention also exhibit the ability to follow the contour of the vessel being treated while still exhibiting the rigidity needed for firm anchoring once the device is deployed by expanding same in place within the vessel.

In summary, the present invention accomplishes advantages and advances in the endoprosthesis art by an endoprosthesis constructed of a malleable strand having bendable segments organized in an undulating fashion, which undulating strand is wound in a generally helical configuration to form the body of the stent portion of the endoprosthesis, same being composed of a plurality of full circle windings continuous with each other along the helical path. In general, the undulations of adjoining windings generally line-up with one another to either contact one another or be closely spaced from one another. At selected ones of these locations, welds are applied in other to thereby join adjacent windings. The selected locations are such as to join adjacent end windings, preferably along a plurality of spinal weld patterns that follow the contour of the adjacent windings. A graft component covers the central length of the stent component while a substantial portion of the welded end lengths protrude longitudinally beyond the graft component. Graft materials sandwich the central portion of the stent component between inner and outer walls of graft material. In an especially preferred embodiment for manufacturing the endoprosthesis, the inner graft member is spun onto a mandrel, the formed and welded stent component is placed thereover, and an outer graft member is spun over the central length of the stent component in a manner to effect adherence of the inner and outer graft members together to capture the stent member therebetween.

It is accordingly a general object of the present invention to provide an improved endoprosthesis having a graft component at its central portion and a welded stent component at its ends, as well as the making and use of same.

Another object of the present invention is to provide an improved endoprosthesis for percutaneous placement that addresses management of independent vascular dissections, aneurysms, and other vascular or ductal malformations.

Another object of this invention is an improved endoprosthesis and procedure for deploying same which includes anchoring uncovered stent ends within a body vessel wall.

Another object of the present invention is to provide an improved endoprosthesis of enhanced patency which minimizes the risk of developing intimal hyperplasia upon deployment within a living vessel, and the method associated therewith.

Another object of this invention is to provide an improved endoprosthesis and deployment procedure whereby stent spines add rigidity to endoprosthesis ends and maintain the position and patency of the graft of the endoprosthesis.

Another object of the present invention is to provide an improved endoprosthesis and deployment procedure incorporating a balloon expandable device and which is delivered through a push tube or similar system to facilitate delivery to the treatment location.

Another object of the present invention is to provide endoprostheses suitable for vascular, bronchial, tracheal, urological, rectal, transinterhepactic shunting, bilary tree uses, and the like.

Another object of this invention is to provide an endoprosthesis especially well-suited for use in aortic or abdominal applications.

These and other objects, features and advantages of this invention will be clearly understood through a consideration of the following detailed description.

BRIEF DESCRIPTION OF THE DRAWINGS

This invention is further elucidated in the following description with reference to the annexed drawings, wherein:

FIG. 1 is a perspective view of a portion of a balloon catheter having an endoprosthesis in accordance with the present invention positioned thereon for subsequent deployment;

FIG. 2 is a somewhat schematic view illustrating a step during the preparation of a particular embodiment of the endoprosthesis;

FIG. 3 is an elevational view illustration of a step subsequent to FIG. 2 in the embodiment of the illustrated manufacturing procedure;

FIG. 4 is an elevational view of a completed endoprosthesis and a subsequent step in the embodiment of the illustrated process; and FIG. 5 is a cross-sectional view along the line 5—5 of FIG. 4.

DESCRIPTION OF THE PARTICULAR EMBODIMENTS

An endoprosthesis in accordance with the present invention is generally designated at 11 and FIG. 1, shown positioned over a balloon component 12 of a catheter 13 of generally known construction. The balloon is illustrated in a deflated condition, with the endoprosthesis closely lying thereover. As is well known in the art, when a suitable fluid such as saline solution is passed into the catheter under pressure, the balloon component 12 expands, thereby radially expanding the endoprosthesis 11. Typically, this expansion is carried out within a body vessel, such as within a blood vessel, coronary passageway, bilary duct or other body vessel.

Expansion is initiated after the balloon and endoprosthesis are positioned within the vessel so as to be radially spaced away from a diseased or damaged area of the vessel. Upon radial expansion as described, the balloon deploys the endoprosthesis to engage, support and/or repair the diseased damaged, or malformed vessel, passageway or duct. It has been found that the effectiveness of this deployment procedure is particularly enhanced when the endoprosthesis traverses a length greater than the length of the damaged, diseased or malformed section so that there is an overlap to enable anchoring portions of the endoprosthesis to extend beyond each end of the diseased, damaged or malformed sections of the vessel. When the endoprosthesis is deployed, these anchoring sections will thus engage relatively healthy portions of the vessel wall. In this regard, the deployment procedure according to the invention preferably includes providing the endoprosthesis having a length greater than the length of the diseased, damaged or malformed section of the vessel when the endoprosthesis is positioned along this area, taking into consideration changes in contour of the vessel at this section. One or more hooks or barbs 31 (FIG. 4) may be included to ensure the endoprosthesis will remain at the location in the vessel at which it was deployed.

With more particular reference to the endoprosthesis 11, the illustrated embodiment includes a stent component 21 constructed of a strand of metal or polymer which exhibits malleability adequate to be formed into shapes such as those illustrated, retain those shapes, and expand as discussed herein when subjected to radial outwardly directed forces. In the illustrated embodiment, the strand is formed into bendable segments to provide a repeating pattern of undulations. The undulating strand is shaped into a plurality of full circle windings 14 that are wrapped through 360°. Each winding includes a plurality of bendable segments 25, generally designated 15. Each bendable segment includes legs 16 joined by a connecting portion 17. In the embodiment shown in the drawings, legs 16 and connecting portions 17 define a sinusoidal curve which can be shaped as illustrated in the drawings or take on somewhat different shapes. In this regard, and with regard to the manner in which the undulating winding can be formed, reference is made to Pinchuk U.S. Pat. Nos. 5,019,090 and No. 5,092,877, the subject matter thereof being incorporated by reference hereinto.

A plurality of welds 18 join adjacent pairs of connecting portions 17 at each end length 19, 20 of the endoprosthesis. In accordance with the invention, at least one weld 18 joins each winding of each end length 19, 20. It will be noted that these welds 18 preferably form somewhat of a pattern or spine joining the windings of each end length 19, 20. This pattern or spine has a pitch angle "A" which follows the pitch angle defined by adjacent connecting portions 17 of the adjacent windings defining each end length. A plurality of such weld groups or spines are spaced generally circumferentially along the end lengths of the endoprosthesis. For example, as illustrated in FIG. 3, a grouping or spine of four welds 18a, 18b, 18c and 18d are shown. It is understood that similar groupings continue along the circumference of the endoprosthesis. Each such grouping or spine generally follows pitch angle "A", which substantially follows the graft helix that is defined by adjacent connecting portion pairs 17, 17 of adjacent windings.

It will be appreciated that during expansion, each of the bendable segments 15 will open such that each leg 16 is spaced farther from legs adjoining same than prior to expansion. Each weld 18 remains along the pattern or spine, except the pitch angle "A" is greater than or steeper than, for example, the pitch angle "A" shown in FIG. 3 prior to the expansion.

As depicted in the illustrated embodiment, each spine can be spaced from its adjoining spine by groupings of unwelded bendable segments, which grouping generally follow the pitch angle "A". One such unwelded grouping is presented between the welded groupings as illustrated in the preferred embodiment. Generally speaking, the larger the circumference of the stent member, the greater the number of weld spines can be accommodated. Different spacings are also possible. It will be appreciated that the greater the number of weld spines, the greater the rigidity of the end lengths 19, 20. More rigid end lengths will require more force to expand and will provide anchoring portions of the endoprosthesis which possess greater hoop strength than unwelded end portions, thereby making less likely unintentional movement of the endoprosthesis once it has been deployed within a vessel.

While the illustrated embodiment shows the plurality of welds oriented in a helical manner along a generally continuous pathway or helical spine, other weld orientations are also possible. For example, one of the weld spines of a multiple-spine configuration can omit welds therealong, such that every other adjacent pair of connecting portions along this interrupted helical spine can remain unwelded. Alternating connecting portion adjacent pairs can remain unwelded, preferably staggered in such a manner that each adjacent winding is secured together at its other adjacent winding or windings by at least one weld at a connecting portion pair. It is possible to form helical spines in an orientation other than that as illustrated which follows the pitch angle of the helix, for example weld spine patterns that are generally parallel to the axis of the endoprosthesis and weld spine patterns that follow a counter-clockwise oriented helix, rather than the clockwise oriented helical spine illustrated in the drawings.

Welding as generally discussed herein achieves substantially uniform expansion when these endoprostheses are deployed. By following the pitch angle of the wrapped helix of the endoprosthesis, and by providing weld spine patterns that provide a weld at each connecting portion pair therealong, a particularly even pull is experienced on each leg 16 when the endoprosthesis is expanded for deployment. Particularly uniform stretching is experienced, which is important to the operative functional advantages of the endoprostheses according to the invention.

More specifically, it is at present generally accepted that the supporting surface area (typically the "metal" outside or working surface of the stent) is to constitute between about 12% and about 15% of the cylindrical surface defined by the stent. Otherwise, inadequate support will be provided. This means that, under present beliefs, it is desirable to have between about 85% and about 88% open space presented by the external cylindrical definition of a stent component. The configuration of the welded end portions of the stent component of the invention is tailored to fall within these guidelines. More importantly, the amount of supportive surface area or "metal" presented to the vessel by the stent is a consistent percentage throughout the length and circumference of the welded ends. Accordingly, if 12 to 15% supporting surface area is provided by the welded ends, all portions of their cylindrical surfaces, both before expansion and when expanded as deployed, present a supporting surface area within this percentage range. This uniformity of supporting surface is important. This feature, for example, avoids the undesirable situation where the 12 to 15% guideline is met when the entirety of the surface is averaged, but might be considerably below the guideline percentage at the very location where support is most needed. Similarly, if certain locations present too great a percent of support surface or metal, accelerated hyperproliferation could occur, resulting in cell growth that is thicker than desired at these locations of excess support surface, resulting in a narrowing of the body passageway at this location.

With more particular reference to the welds 18 of the stent component 21 of the endoprosthesis, they are preferably formed by a fusion welding procedure, such as electron beam welding, laser welding, TIG welding and the like. Welding in inert gas environments or under vacuum conditions is particularly desirable for materials such as tantalum which have a great affinity for oxygen, hydrogen and the like in that metals actively absorb gases such as oxygen. Accordingly, when welding is carried out in the presence of even small amounts of oxygen or other gases having a strong affinity for tantalum or the like, an embrittlement at the weld is experienced. It is believed that the onset of such embrittlement conditions is especially likely during an operation such as fusion welding wherein a metal is rapidly heated and quickly cooled thereafter. The welds according to the present invention are preferably carried out within an enclosure which provides a consistent environment of inert gas such as argon, helium or other members of the inert gas family including those specified in the inert gas grouping of the periodic table. It is especially preferred that the inert gas be contained within the enclosed compartment during welding and that the compartment be filled with inert gas, as opposed to a situation where inert gas is directed by means of a gas flow past an open welding area. It has been found to be important to maintain the inert gas environment within the compartment while preventing influx of air or other oxygen source. The fusion welding energy source typically is directed onto the location of the connecting portion pairs.

Strand material out of which the stent component 21 of the endoprosthesis according to the invention is made must be capable of forming a joint under welding or heating conditions. In addition, the strand material should have malleability characteristics. Included are tantalum, titanium, silver, gold, Nitinol alloy, stainless steel, annealed elastic metal materials, and alloys containing same. Polymers may also be used, such as polyether sulfone, polyimides, polycarbonates, polypropylenes, high molecular weight polyethylenes, carbon fibers, Kevlar polymer, and the like. It is also possible to coat these materials after stent formation has been completed with porous or textured surfaces for cellular ingrowth and the like or with non-thrombogenic agents such as pyrolytic carbon, heparin, hydrogels, Teflon materials, silicones, polyurethanes and the like. Treatments can also be carried out so that drugs or medicines can be eluted therefrom. It is also possible. that certain stent components may be made of biodegradable materials. The strand material must, of course, be biocompatible. Tantalum is the especially preferred strand material. For example, materials such as tantalum have the ability to be plastically deformed without significantly compromising the strength of the metal. Such a property is typically not provided by more elastic materials such as stainless steel which, once bent, will lose a noticeable percentage of its strength.

In addition to the stent component 21, endoprostheses in accordance with the present invention include a graft component, generally designated as 22 in FIG. 4. Graft component 22 includes both an interior graft member 23 and an exterior graft member 24. The interior and exterior graft members typically have the same longitudinal length, although the exterior graft member 24 could be longer than the interior graft member 23 if desired. In essence, the interior graft member serves as an attachment base for the exterior graft member to incorporate the stent member therebetween.

While the graft component could be made of various different materials and in various different configurations, such as those which are woven, non-woven, spun, molded, extruded and the like, the preferred graft component has a non-woven, spun configuration. It is especially preferred that this material be made by a winding procedure such as that generally described in Wong U.S. Pat. No. 4,475,972, incorporated by reference hereinto. This winding procedure is generally illustrated in FIG. 2. A mandrel 25 is arranged for rotation by a suitable device such as the illustrated motor 26. A shuttle assembly 27 is positioned so as to slide back and forth generally parallel to the mandrel, as illustrated by the double-headed arrow. A single- or multiple-nozzle ejector 28 supplies freshly extruded strands of polymer from each nozzle thereof, which strands are positioned onto the mandrel 25 or strands of polymer previously laid down onto the mandrel by the ejector 28. A supply of spinnable polymer 29 is also shown as feed to the multiple-nozzle ejector 28. The combination of the rotating mandrel and reciprocating shuttle assembly forms the non-woven graft material illustrated wherein individual strands cross underlying strands. It will be appreciated that the spinnable polymer freshly extruded through the nozzles will lie down over and be generally adhered to underlying strands which had been previously laid down, particularly those which cross each other.

It is also possible to lay down these strands in a single helical pattern. In that event, an ejector having enough nozzles to lay down a ribbon formed of these strands during one pass can be used to lay down a helical internal ribbon in which event the shuttle would not be used. Whether a single helical pattern is used or crossing helical patterns are used, typically the pitch angle of the single helical pattern or of one of the helical patterns will approximate the pitch angle of the stent component. When the endoprosthesis is expanded, these pitch angles will accordingly enlarge, generally to about the same extent.

In the illustrated embodiment, the interior graft member 23 is first formed on the mandrel in accordance with the procedure illustrated in FIG. 2. Thereafter, the stent component 21 is fitted thereover. Typically, this can include trimming the interior graft member 23 to the desired length, after which the stent component is slid thereover while the graft member 23 is still on the mandrel. This approach is convenient for formation of the exterior graft member 24 directly onto the same mandrel by following substantially the same procedure as illustrated in FIG. 2. When thus laid down, it is preferred that the inner graft member strands and especially the outer graft member strands are not fully cured. As a result, bonding takes place between the strands of the inner and outer members throughout the length of the center of the stent component. The central length of the stent component is enveloped in or captured by the graft component 22 as generally shown in FIGS. 4 and 5. After assembly is complete, the edges of the graft component are preferably trimmed.

It is desired that the graft component overlap with the end lengths 19, 20 of the stent component. Preferably this overlap is such that a maximum of approximately twenty-five percent of the welds 18 of these end lengths are covered by the inner and outer graft material. This insures that the combination will be held together without buckling or pleating. Enough of the welded end lengths are to be uncovered, at least by the exterior graft member 24, so that a substantial portion of the end lengths expand without any significant constraint by the graft component to ensure full and uniform deployment of the welded end lengths as discussed herein. Superior stenting and anchoring result. In addition, a sufficient extent of the end lengths of the stent, component should be uncovered by the graft materials to facilitate having the graft ends maintain patency and proper endoprosthesis positioning. Uses in abdominal or aortic applications are especially suitable for these types of endoprostheses.

Materials suitable for making the graft component include polytetraethylene (PTE), EPTE, polytetrafluoroethylene, nylons, polyamides, as well as other polymers such as Gortex and Dacron fibers, bioabsorbables and other biocompatible materials. The interior and exterior members may be of the same or different materials. Treatment materials such as drugs and anticoagulants may be incorporated, especially on the exterior graft member. When the graft component is to be a spun fiber component, it is important that the polymer be fiber forming in air so as to be suitable for delivery in an apparatus as generally illustrated in FIG. 2 and/or be suitable for bonding in place upon spinning one layer of fibers onto another.

The formed graft component preferably is compliant enough to be able to readily follow the stent component, especially during its expansion, while also being of low elasticity so as to not significantly interfere with the ability of the stent component to maintain the endoprosthesis in its deployed condition. For example, a recoil of not greater than about 7 percent, preferably between about 5 and about 7 percent is suitable for a preferred graft material. Should the material exhibit inadequate compliance or excessive recoil or elasticity, the components of the endoprosthesis will tend to separate from one another, and/or develop ripples. Preferably, the graft member moves through its plastic state, or is plastically deformed, during endoprosthesis deployment so it will be stretched and expanded by the stent component and remain so after implantation is complete. Also graft structures, such as meshes, can exhibit elasticity due to the pattern of the fibrils. Whatever the graft member structure or material, the recoil force exerted on the stent component cannot be greater than the magnitude of radial force which will deform or collapse the stent component.

As discussed herein, the endoprosthesis of the invention can be deployed by means of a balloon catheter. Alternatively, the stent component and hence the endoprosthesis can be self-expanding. Such a stent component is made of nickel-titanium alloys or Nitinol alloys, or other materials which rapidly change in configuration or size when a temperature threshold is achieved. For example, a self-expanding endoprosthesis having a stent made of Nitinol alloy can be deployed into a blood vessel at an implantation diameter. When the treatment site is reached, either body temperature or the injection of a saline solution at a greater temperature will cause the endoprosthesis to rapidly open or "pop" to a larger diameter which is the diameter associated with full deployment of the endoprosthesis so as to treat the stenosis or the like.

It will be understood that the embodiments of the present invention which have been described are illustrative of some of the applications of the principles of the present invention. Numerous modifications may be made by those skilled in the art without departing from the true spirit and scope of the invention.

I claim:

1. A method for forming an implantable transluminal endoprosthesis, comprising the steps of:

providing an elongated strand of malleable material, forming said strand into a repeating pattern of undulations having repeating bendable connecting portions, wrapping the strand with the repeating pattern of undulations to follow a generally helical axis having a plurality of full circle windings which are substantially continuous with each other along the generally helical axis until the bendable connecting portions of one of the full circle windings are generally adjacent to respective bendable connecting portions of an adjacent full circle winding to define a plurality of adjacent pairs of bendable connecting portions to thereby form a stent component having an interior surface and an exterior surface, said stent component having a central length portion between two end length portions, each said end length portion having a plurality of said full circle windings;

welding together a plurality of said pairs of connecting portions of adjacent said full circle windings of the end length portions to form two welded end lengths; and positioning a graft component along said interior and exterior surfaces of the stent component, including overlying an inner and outer member of the graft component over less than the entirety of the interior and exterior surfaces, respectively, of the stent component, said positioning step exposing a substantial axially extending length of each of said two welded end length portions of the stent component such that the thus exposed welded end length portions are uncovered by the graft component, and said overlying of the positioning step includes overlying at least one welded full circle winding of both of said welded end lengths.

2. The method in accordance with claim 1, wherein said step of positioning a graft component includes incorporating a central length of the stent component between the inner and outer members of the graft component and adhering said inner and outer members together.

3. The method in accordance with claim 1, wherein said positioning step includes overlying not greater than approximately one quarter of the length of each of said two welded end lengths.

4. The method in accordance with claim 1, wherein said positioning step includes winding a plurality of fibers over said central length portion of the stent component.

5. The method in accordance with claim 1, wherein said welding step includes fusion welding.

6. The method in accordance with claim 1, wherein said welding step is carried out with an enclosed atmosphere of inert gas.

7. The method in accordance with claim 1, wherein said positioning step includes winding a plurality of fibers over a mandrel and positioning thereover said central length portion of the stent component.

8. The method in accordance with claim 1, wherein said positioning step includes winding a plurality of fibers over a mandrel and positioning thereover said central length portion of the stent component, and said positioning step further includes winding a further plurality of fibers over said central length portion of the stent component.

* * * * *

UNITED STATES PATENT AND TRADEMARK OFFICE
CERTIFICATE OF CORRECTION

PATENT NO. : 5,824,043
DATED : October 20, 1998
INVENTOR(S) : Robert J. Cottone, Jr.

It is certified that error appears in the above-identified patent and that said Letters Patent is hereby corrected as shown below:

Col. 1, line 60, "angioplasy" should read --angioplasty--.
Col. 3, line 34, "at 11 and" should read --at 11 in--;
    line 49, insert a comma --,-- after "diseased".
Col. 4, line 48, "grouping" should read --groupings--.
Col. 6, line 28, "possible. that" should read --possible that--.
Col. 7, line 49, delete the comma "," after "stent".

Signed and Sealed this

Twenty-fifth Day of July, 2000

Attest:

Q. TODD DICKINSON

Attesting Officer

Director of Patents and Trademarks